US007041456B2

(12) United States Patent
Barnett et al.

(10) Patent No.: US 7,041,456 B2
(45) Date of Patent: May 9, 2006

(54) DETECTION OF WHEAT AND BARLEY FUNGAL PATHOGENS WHICH ARE RESISTANT TO CERTAIN FUNGICIDES USING THE POLYMERASE CHAIN REACTION

(75) Inventors: Charles Jason Barnett, Research Triangle Park, NC (US); James Joseph Beck, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 573 days.

(21) Appl. No.: 10/401,343

(22) Filed: Mar. 27, 2003

(65) Prior Publication Data

US 2003/0194735 A1 Oct. 16, 2003

Related U.S. Application Data

(60) Provisional application No. 60/369,796, filed on Apr. 3, 2002.

(51) Int. Cl.
*C12Q 1/68* (2006.01)

(52) U.S. Cl. .......................................................... 435/6

(58) Field of Classification Search ..................... None
See application file for complete search history.

(56) References Cited

U.S. PATENT DOCUMENTS

| | | | | |
|---|---|---|---|---|
| 5,585,238 | A | 12/1996 | Ligon et al. | 435/6 |
| 5,800,997 | A | 9/1998 | Beck | 435/6 |
| 5,827,695 | A | 10/1998 | Beck | 435/91.2 |
| 6,221,595 | B1 | 4/2001 | Beck et al. | 435/6 |
| 6,319,673 | B1 | 11/2001 | Beck et al. | 435/6 |
| 6,358,680 | B1 | 3/2002 | Beck | 435/6 |
| 6,485,907 | B1 | 11/2002 | Beck et al. | 435/6 |
| 6,599,701 | B1 | 7/2003 | Honeycutt et al. | |
| 6,645,720 | B1 | 11/2003 | Barnett et al. | 435/6 |
| 6,733,972 | B1 | 5/2004 | Barnett et al. | 435/6 |

OTHER PUBLICATIONS

Cavelier et al, Résistance de *Pseudocerosporella herpotrichoides* aux benzimidazoles et thiophanates chez le blé d'hiver en France *Bulletin of the Organization European for the Protection of Plants*, vol. 85 (1985) pp. 495-502 [Abstract provided in English on p. 501].

Dyer et al, Genetic Control of Resistance to the Sterol 14α-Demethylase Inhibitor Fungicide Prochloraz in the Cereal Eyespot Pathogen *Tapesia yallundae Applied and Environmental Microbiology*, vol. 66 (2000), pp. 4599-4604.

Leroux & Gredt, Evolution of Fungicide Resistance in the Cereal Eyespot Fungi *Tapesia yallundae* and *Tapesia acuformis* in France *Pesticide Science*, vol. 51 (1997), pp. 321-327.

Leroux and Cavelier, Phénoménes de Résistance du Piétin-Verse Aux Benzimidazoles et Aux Thiophanates *Phytoma*, vol. 351 (1983) pp. 40-47.

Schesser et al, Use of Polymerase Chain Reaction to Detect the Take-All Fungus, *Gaeumannomyces graminis*, in Infected Wheat Plants *Applied and Environmental Microbiology*, vol. 57, (1991) pp. 553-556.

*Primary Examiner*—Jeffrey Fredman
*Assistant Examiner*—Heather G. Calamita
(74) *Attorney, Agent, or Firm*—Mary Kakefuda

(57) ABSTRACT

Primers specific for races of pathogenic fungi which are resistant to certain fungicides are used in polymerase chain reaction assays for the detection of fungal pathogens. The use of these primers enables the detection of specific isolates of fungal pathogens and the monitoring of disease development in plant populations. The invention includes DNA sequences which show variability between different fungal pathotypes. Such DNA sequences are useful in the method of the invention as they can be used to derive primers for use in polymerase chain reaction (PCR)-based diagnostic assays. These primers generate unique fragments in PCR reactions in which the DNA template is provided by specific fungal pathotypes and can thus be used to identify the presence or absence of specific pathotypes in host plant material before the onset of disease symptoms.

8 Claims, No Drawings

DETECTION OF WHEAT AND BARLEY FUNGAL PATHOGENS WHICH ARE RESISTANT TO CERTAIN FUNGICIDES USING THE POLYMERASE CHAIN REACTION

This application claims the benefit of U.S. Provisional Patent Application Ser. No. 60/369,796 filed Apr. 3, 2002, which is incorporated by reference in its entirety.

FIELD OF THE INVENTION

The present invention relates to the use of primers specific for races of pathogenic fungi which are resistant to certain fungicides in polymerase chain reaction assays for the detection of fungal pathogens. The use of these primers enables the detection of specific isolates of fungal pathogens and the monitoring of disease development in plant populations.

BACKGROUND OF THE INVENTION

Diseases in plants cause considerable crop loss from year to year resulting both in economic deprivation to farmers and additionally in many parts of the world to shortfalls in the nutritional provision for local populations. The widespread use of fungicides has provided considerable security against plant pathogen attack. However, despite $1 billion worth of expenditure on fungicides, worldwide crop losses amounted to approximately 10% of crop value in 1981 (James, 1981; *Seed Sci. & Technol.* 9: 679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains which are resistant to particular fungicides. As early as 1981, Fletcher and Wolfe (1981; *Proc.* 1981 *Brit. Crop Prot. Conf.*) contended that 24% of the powdery mildew populations from spring barley, and 53% from winter barley showed considerable variation in response to the fungicide triadimenol and that the distribution of these populations varied between varieties with the most susceptible variety also giving the highest incidence of less susceptible types. Similar variation in the sensitivity of fungi to fungicides has been documented for wheat mildew (also to triadimenol), *Botrytis* (to benomyl), *Pyrenophora* (to organomercury), *Tapesia* (to MBC-type fungicides) and *Mycosphaerella fijiensis* to triazoles to mention just a few (Jones and Clifford; Cereal Diseases, John Wiley, 1983).

Cereal species are grown world-wide and represent a major fraction of world food production. Although yield loss is caused by many pathogens, the necrotizing pathogens *Septoria* and *Tapesia* are particularly important in the major cereal growing areas of Europe and North America (Jones and Clifford; Cereal Diseases, John Wiley, 1983). In particular, the differential symptomology caused by different isolates and species of these fungi make the accurate predictive determination of potential disease loss difficult. Consequently, the availability of improved diagnostic techniques for the rapid and accurate identification of specific pathogens will be of considerable use to field pathologists.

The eyespot disease of cereals is caused by the fungi *Tapesia yallundae* and *Tapesia acuformis* is restricted to the basal culm of the plant. The two causal pathogens were previously classified as two subspecies of *Pseudocercosporella herpotrichoides* (Fron) Deighton (anamorph). *T. yallundae* refers to the variety herpotrichoides and the SF-,L-,I- or W-types. *T acuformis* corresponds to the variety acuformis and the FE-, N-, II- or R-types (Leroux and Gredt, 1997; 51:321–327). Wheat, rye, oats and other grasses are susceptible to the eyespot disease which occurs in cool, moist climates and is prevalent in Europe, North and South America, Africa and Australia. Wheat is the most susceptible cereal species, but isolates have been identified which are also virulent on other cereals. The R-strain (*T. acuformis*) of the fungus, for example, has also been isolated from rye and grows more slowly on wheat than the W-strain (*T. yallundae*) which has been isolated from wheat. Although eyespot may kill tillers or plants outright, it more usually causes lodging and/or results in a reduction in kernel size and number. Yield losses associated with eyespot are of even greater magnitude than those associated with *Septoria tritici* and *Septoria nodorum.* Typical control measures for eyespot include treatment with growth regulators to strengthen intemodes, and fungicide treatment. However, the differing susceptibility of cultivars to different strains of the fungus render the predictive efficacy of fungicide treatments difficult. In addition, both Leroux et al (1997; *Pesticide Science,* 51:321–327) and Dyer et al (2000; *Appl. and Environ. Microbiol.* 66:4599–4604) have reported on isolates of *T. yallundae* with reduced sensitivity to the imidazole DMI fungicide prochloraz (1-[N-propyl-N-[2-92,4,6-trichlorophenoxy)ethyl]carbamoyl]-imidazole). Following heavy treatments of benzimidazole fungicides such as benomyl, carbendazim and thiabendazole, acquired resistance to this class of fungicides was determined in both *T. acuformis* and *T. yallundae* (Leroux and Cavelier, 1983; *Phytoma* 351:40) and (Cavelier et al, 1985; *Bull. OEPP* 85:495).

Thus, there is a real need for the development of technology which will allow the identification of specific races of pathogen fungi which are resistance to certain fungicides early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

SUMMARY OF THE INVENTION

The present invention relates to the use of primers specific for races of pathogenic fungi which are resistant to certain fungicides in polymerase chain reaction assays for the detection of fungal pathogens. The invention provides DNA sequences which show variability between different fungal pathotypes. Such DNA sequences are useful in the method of the invention as they can be used to derive primers for use in polymerase chain reaction (PCR)-based diagnostic assays. These primers generate unique fragments in PCR reactions in which the DNA template is provided by specific fungal pathotypes and can thus be used to identify the presence or absence of specific pathotypes in host plant material before the onset of disease symptoms.

This invention provides the possibility of assessing potential damage in a specific crop variety-pathogen strain relationship and of utilizing judiciously the diverse armory of fungicides which is available. Furthermore, it can be used to provide detailed information on the development and spread of specific pathogen races over extended geographical areas.

Kits useful in the practice of the invention are also provided. The kits find particular use in the identification of *Tapesia* pathogens.

The present invention provides a nucleic acid molecule comprising the nucleic acid sequence of SEQ ID NOS: 3–13 or 14. In a more preferred embodiment, the nucleic acid molecule has sequence identity with at least 10 contiguous nucleotides of SEQ ID NOS: 2–13 or 14. In another preferred embodiment, the nucleic acid molecule comprises a nucleotide sequence of SEQ ID NOs: 3–76 or 77.

The invention also provides a pair of oligonucleotide primers wherein at least one primer consists of the nucleotide sequence of SEQ ID NOS: 3–76 or 77. In a preferred embodiment, the pair of oligonucleotide primers comprises:

JB944 (SEQ ID NO:59) and JB943 (SEQ ID NO:58;
JB944 (SEQ ID NO:59) and JB945 (SEQ ID NO:60);
JB934 (SEQ ID NO:49) and JB935 (SEQ ID NO:50); and
JB937 (SEQ ID NO:52) and JB935 (SEQ ID NO:50).

The invention also provides a method for the detection of a fungal pathogen, comprising the steps of:

(a) isolating DNA from a plant tissue infected with a pathogen;
(b) subjecting said DNA to polymerase chain reaction amplification using at least one primer having sequence identity with at least 10 contiguous nucleotides of a randomly amplified polymorphic DNA sequence of a *Tapesia* spp.; and
(c) detecting said fungal pathogen by visualizing the product or products of said polymerase chain reaction amplification.

In a preferred embodiment, the fungal pathogen is *Tapesia yallundae, Tapesia acuformis.* More preferably, the *Tapesia yallundae* is subtype Ic., and *Tapesia acuformis* subtypes IIs or IIp. In another preferred embodiment, at least one primer having the nucleotide sequence of SEQ ID NOS: 3–76 or 77.

The invention further provides a method for the detection of a fungal pathogen, comprising the steps of:

(a) isolating DNA from a plant tissue infected with a pathogen;
(b) subjecting said DNA to polymerase chain reaction amplification using at least one primer having sequence identity with at least 10 contiguous nucleotides of a randomly amplified polymorphic DNA from a *Tapesia* spp.; and
(c) detecting said fungal pathogen by visualizing the product or products of said polymerase chain reaction amplification.

In a preferred embodiment, the fungal pathogen is *Tapesia yallundae, Tapesia acuformis.* More preferably, the *Tapesia yallundae* is subtype Ic, and *Tapesia acuformis* subtypes IIs or IIp. In another preferred embodiment, at least one primer having the nucleotide sequence of SEQ ID NOS: 3–76 or 77. In more preferred embodiment, the pair of primers comprises:

JB944 (SEQ ID NO:59) and JB943 (SEQ ID NO:58;
JB944 (SEQ ID NO:59) and JB945 (SEQ ID NO:60);
JB934 (SEQ ID NO:49) and JB935 (SEQ ID NO:50); or
JB937 (SEQ ID NO:52) and JB935 (SEQ ID NO:50).

The invention also provides a diagnostic kit used in detecting a fungal pathogen comprising at least one primer having at least 10 contiguous nucleotides of a nucleic acid molecule of the nucleic acid molecules described above. In a preferred embodiment, at least one primer comprises SEQ ID NO: 3–76 or 77. In more preferred embodiments, the pair of primers are:

JB944 (SEQ ID NO:59) and JB943 (SEQ ID NO:58;
JB944 (SEQ ID NO:59) and JB945 (SEQ ID NO:60);
JB934 (SEQ ID NO:49) and JB935 (SEQ ID NO:50); or
JB937 (SEQ ID NO:52) and JB935 (SEQ ID NO:50).

Brief Description of the Sequences in the Sequence Listing

| | |
|---|---|
| SEQ-ID-NO: 1 | M13 Sequencing Forward Primer |
| SEQ-ID-NO: 2 | M13 Sequencing Reverse Primer |
| SEQ-ID-NO: 3 | RAPD-PCR Clone Ib1-27 |
| SEQ-ID-NO: 4 | RAPD-PCR Clone Ib2-31 |
| SEQ-ID-NO: 5 | RAPD-PCR Clone Ib3-33 |
| SEQ-ID-NO: 6 | RAPD-PCR Clone Ic1-22 |
| SEQ-ID-NO: 7 | RAPD-PCR Clone Ic 020502Ic4and6 |
| SEQ-ID-NO: 8 | RAPD-PCR Clone Ic 020602D-20 |
| SEQ-ID-NO: 9 | RAPD-PCR Clone Ic 020602D-21 |
| SEQ-ID-NO: 10 | RAPD-PCR Clone IIp1-17 |
| SEQ-ID-NO: 11 | RAPD-PCR Clone IIp 020602A-11 |
| SEQ-ID-NO: 12 | RAPD-PCR Clone IIp 020602B-15 |
| SEQ-ID-NO: 13 | RAPD-PCR Clone IIp 020602B-16 |
| SEQ-ID-NO: 14 | RAPD-PCR Clone IIs2-39 |
| SEQ-ID-NO: 15 | JB900 |
| SEQ-ID-NO: 16 | JB901 |
| SEQ-ID-NO: 17 | JB902 Probe |
| SEQ-ID-NO: 18 | JB903 |
| SEQ-ID-NO: 19 | JB904 |
| SEQ-ID-NO: 20 | JB905 |
| SEQ-ID-NO: 21 | JB906 |
| SEQ-ID-NO: 22 | JB907 |
| SEQ-ID-NO: 23 | JB908 |
| SEQ-ID-NO: 24 | JB909 |
| SEQ-ID-NO: 25 | J8910 |
| SEQ-ID-NO: 26 | 1B911 |
| SEQ-ID-NO: 27 | JB912 Probe |
| SEQ-ID-NO: 28 | JB913 |
| SEQ-ID-NO: 29 | JB914 |
| SEQ-ID-NO: 30 | JB915 |
| SEQ-ID-NO: 31 | JB916 |
| SEQ-ID-NO: 32 | J8917 Probe |
| SEQ-ID-NO: 33 | JB918 |
| SEQ-ID-NO: 34 | JB919 |
| SEQ-ID-NO: 35 | JB920 |
| SEQ-ID-NO: 36 | JB921 |
| SEQ-ID-NO: 37 | JB922 Probe |
| SEQ-ID-NO: 38 | JB923 |
| SEQ-ID-NO: 39 | JB924 |
| SEQ-ID-NO: 40 | JB925 |
| SEQ-ID-NO: 41 | JB926 |
| SEQ-ID-NO: 42 | JB927 Probe |
| SEQ-ID-NO: 43 | JB928 |
| SEQ-ID-NO: 44 | JB929 |
| SEQ-ID-NO: 45 | JB930 |
| SEQ-ID-NO: 46 | JB931 |
| SEQ-ID-NO: 47 | JB932 |
| SEQ-ID-NO: 48 | JB933 |
| SEQ-ID-NO: 49 | JB934 |
| SEQ-ID-NO: 50 | JB935 |
| SEQ-ID-NO: 51 | JB936 |
| SEQ-ID-NO: 52 | JB937 |
| SEQ-ID-NO: 53 | JB938 |
| SEQ-ID-NO: 54 | JB939 |
| SEQ-ID-NO: 55 | JB940 |
| SEQ-ID-NO: 56 | JB941 |
| SEQ-ID-NO: 57 | JB942 |
| SEQ-ID-NO: 58 | JB943 |
| SEQ-ID-NO: 59 | JB944 |
| SEQ-ID-NO: 60 | JB945 |
| SEQ-ID-NO: 61 | JB946 |
| SEQ-ID-NO: 62 | JB947 |
| SEQ-ID-NO: 63 | JB948 |

-continued

| Brief Description of the Sequences in the Sequence Listing | |
|---|---|
| SEQ-ID-NO: 64 | JB949 |
| SEQ-ID-NO: 65 | JB950 |
| SEQ-ID-NO: 66 | JB951 |
| SEQ-ID-NO: 67 | JB952 |
| SEQ-ID-NO: 68 | JB953 |
| SEQ-ID-NO: 69 | JB954 |
| SEQ-ID-NO: 70 | JB955 |
| SEQ-ID-NO: 71 | JB956 |
| SEQ-ID-NO: 72 | JB957 |
| SEQ-ID-NO: 73 | JB958 |
| SEQ-ID-NO: 74 | JB959 |
| SEQ-ID-NO: 75 | JB960 |
| SEQ-ID-NO: 76 | JB961 |
| SEQ-ID-NO: 77 | JB962 |

DETAILED DESCRIPTION OF THE INVENTION

The present invention provides unique DNA sequences which are useful in identifying different pathotypes of plant pathogenic fungi. Particularly the DNA sequences can be used as primers in PCR based analysis for the identification of fungal pathotypes. The DNA sequences of the invention include products cloned from RAPD primer analysis of particular fungal pathogens as well as primers which are derived from these regions which are capable of identifying the particular pathogen. These DNA sequences from different pathotypes within a pathogen species or genus which vary between the different members of the species or genus based on different fungicides' susceptibility can be used to identify those specific members.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen mitochondrial genome (Schlesser et al., 1991; *Applied and Environ. Microbiol.* 57: 553–556) and random amplified polymorphic DNA (i.e. RAPD) markers were able to distinguish numerous races of *Gremmeniella abietina,* the causal agent of scleroderris canker in conifers.

The DNA sequences of the invention are from randomly amplified polymorphic DNA (RAPD) of different plant pathogens. The RAPD sequences from different pathotypes within a pathogen species or genus vary between the different members of the species or genus. Once having determined the unique RAPD sequences of a pathogen, primers can be derived from the sequences. That is, primers can be designed based on regions within the uniquely identified RAPD fragment sequence among the fungal pathotypes. These sequences and primers based on these sequences can be used to identify specific pathogen members.

Particular DNA sequences of interest include uniquely identified RAPD sequences from *Tapesia,* particularly, *Tapesia acuformis* and *Tapesia yallundae,* more particularly for the identification of *T. acuformis* subtypes IIs and IIp and *T. yallundae* subtypes Ia, Ib and Ic. Such DNA sequences as well as primers of interest are given in SEQ ID NO: 3–77. The sequences find use in the PCR-based identification of the pathotypes of interest.

Sequences from RAPD analysis of uniquely identified fragments include SEQ-ID-NOs: 3–14. The sequences find use in the PCR-based identification of pathogens of interest.

In a preferred embodiment the sequence disclosed as SEQ-ID-NO: 10 is useful in the development of primers for differentiating *T. acuformis* subtypes IIs and IIp. In another preferred embodiment the sequence disclosed as SEQ-ID-NO: 8 is useful in the development of primers for the detection of *T. yallundae* subtype Ic.

Sequences from oligonucleotide primers derived from the uniquely identified RAPD analysis fragments are disclosed as SEQ-ID-Nos: 15–77. In a preferred embodiment, the pair of oligonucleotide primers consists of SEQ-ID-NO: 59 and SEQ-ID-NO: 58 is used for the detection of *T. yallundae* Ic. In another preferred embodiment, the pair of oligonucleotide primers consists of SEQ-ID-NO: 59 and SEQ-ID-NO: 60 is used for the detection of *T. yallundae* Ic. In yet other embodiments, *T. acuformis* subtype IIs can be differentiated from *T. acuformis* subtype IIp using the primer combination consisting of oligonucleotide primers with SEQ-ID-NO: 49 and SEQ-ID-NO: 50 and the primer combination consisting of oligonucleotide primers with SEQ-ID-NO: 52 and SEQ-ID-NO: 50.

The present invention lends itself readily to the preparation of "kits" containing the elements necessary to carry out the process. Such a kit may comprise a carrier being compartmentalized to receive in close confinement therein one or more container means, such as tubes or vials. One of said container means may contain unlabeled or detectably labeled DNA primers. The labeled DNA primers may be present in lyophilized form, or in an appropriate buffer as necessary. One or more container means may contain one or more enzymes or reagents to be utilized in PCR reactions. These enzymes may be present by themselves or in admixtures, in lyophilized form or in appropriate buffers.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The examples below show, without limitation, typical experimental protocols which can be used in the isolation of unique RAPD sequences, the selection of suitable primer sequences, the testing of primers for selective and diagnostic efficacy, and the use of such primers for disease and fungal isolate detection. Such examples are provided by way of illustration and not by way of limitation.

EXAMPLES

Standard recombinant DNA and molecular cloning techniques used here are well known in the art and are described by J. Sambrook, E. F. Fritsch and T. Maniatis, *Molecular Cloning: A Laboratory manual,* Cold Spring Harbor laboratory, Cold Spring Harbor, N.Y. (1989) and by T. J. Silhavy, M. L. Berman, and L. W. Enquist, *Experiments with Gene Fusions,* Cold Spring Harbor Laboratory, Cold Spring Harbor, N.Y. (1984) and by Ausubel, F. M. et al., *Current Protocols in Molecular Biology,* pub. by Greene Publishing Assoc. and Wiley-Interscience (1987).

Example 1

Fungal Isolates and Genomic Fungal DNA Extraction

See Table 1 for a listing of the fungal isolates used. Isolates for which fungicide sensitivity was characterized were obtained from Institut National de la Recherche Agronomique (INRA, Le Rheu, France). Fungi are grown on PDA (Potato Dextrose Agar) plates. Cultures are incubated for up to 10 days at 28° C. Mycelia are ground in liquid nitrogen, and total genomic DNA is extracted using the following modified CTAB protocol.

1. Freeze-dried mycelium was homogenized in 1.5 ml Eppendorf tubes (two tungsten carbide 3 mm beads were added) using a Retsch mill (MM200, Retsch GmbH & Co., Haan, Germany).
2. Add 600 µl extraction buffer (700 mM NaCl, 50 mM Tris HCl, 10 mM EDTA, 1% β-mercapthoethanol, 1% CTAB) and incubate for 1 hr at 65° C., vortexing every 10–20 minute interval.
3. Add 400 µl chlorophorm:isoamylalcohol (24.1, v:v) shake for 15 min
4. Centrifuge for 10 min (16000 g)
5. Transfer the aqueous phase to a new tube and add 400 µl extraction buffer and 400 µl chloroform:isoamylalcohol
6. Shake for 15 min
7. Centrifuge 10 min
8. Transfer aqueous phase to a new tube
9. Add 0.6× volumes of isopropanol
10. Shake for 5 min
11. Centrifuge for 5 min
12. Discard supernatant and dry pellet
13. Wash pellet with cold EtOH 70%
14. Centrifuge 2 min
15. Dry pellet
16. Resuspend in 50 µl TE

TABLE 1

Identification of Test Isolates

| Fungal Species | Fungal Isolate | Subtype Identifier | Fungicide Sensitivity[1] Triadimenol | Prochloraz | Carbendazim | Cyprodinil (Unix) |
|---|---|---|---|---|---|---|
| *Tapesia yallundae* | 627 N | Ia | S | S | R | S |
| *Tapesia yallundae* | 646 N | Ib | R | S | R | S |
| *Tapesia yallundae* | 572 N | Ic | R | R | R | S |
| *Tapesia yallundae* | 618 N | Ic | R | R | R | S |
| *Tapesia acuformis* | 634 L | IIs | R | S | S | S |
| *Tapesia acuformis* | 643 L | IIs | R | S | S | S |
| *Tapesia acuformis* | 567 L | IIp | R | R | R | S |
| *Tapesia acuformis* | 617 L | IIp | R | R | R | S |
| *Tapesia acuformis* | 626 L | IIp | R | R | R | S |

[1]S = Sensitive,
R = Resistant

Example 2

Amplification of RAPD Products

Polymerase chain reactions are performed to obtain Randomly Amplified Polymorphic DNA (RAPD) profiles for each of the Tapesia spp. subtypes. Forty different RAPD 10-mer primers from Qiagen Operon (Operon Technologies Inc., Alameda, Calif., USA) kits AA and J identified individually as OPAA-01–OPAA-20 and OPJ-01–OPJ-20 are used in amplifications to find RAPD products specific to subtypes Ic and IIp. A single 10-mer RAPD primer is used in RAPD-PCR reactions. Reactions are prepared using the GeneAmp Kit from Perkin-Elmer (Foster City, Calif.; part no. N808-0009) using 50 mM KCl, 2.0 mM $MgCl_2$, 10 mM Tris-HCl, pH8.3 and containing 100 µM of each dTTP, dATP, dCTP, and dGTP in 25 µL reactions. In each reaction, 25 pmol of RAPD primer is used with 0.5 Units of AmpliTaq Polymerase. Approximately 25 ng of genomic DNA from the subtypes listed in Example 1 are used as template. Reactions are run in a GeneAmp Model 9700 thermal cycler (Applied Biosystems, Foster City, Calif.). Thermal cycling is run for 45 cycles of 30 s at 94° C., 30 s at 34° C., and 60 s at 72° C. and is proceeded by a hold at 94° C. for one minute and followed by a final hold at 72° C. for ten minutes before being stored at 4° C. The products are analyzed by loading 10 µl of each PCR sample with loading buffer on a 1.0% agarose gel and electrophoresing.

The gel is stained with ethidium bromide and separated RAPD-PCR bands are observed under ultraviolet light.

Example 3

Selection, Cloning, and Sequencing of Subtype-Specific RAPD-PCR Products

RAPD-PCR products for each *Tapesia* spp. subtype are compared. Bands that appear to be specific to a certain subtype are selected for further analysis by DNA sequencing. These bands are cut from the agarose gel by a sterile scalpel. The RAPD-PCR product is purified from the agarose using GenElute Minus EtBr Spin Columns (Product Code 5-6501, Sigma-Aldrich, St. Louis, Mo., USA). The purified product is cloned into the pCR4-TOPO vector and transformed into One Shot chemically compentent bacterial cells using the TOPO TA Cloning Kit for Sequencing (Invitrogen Corporation, Carlsbad, Calif., USA) under manufacturer's protocol. Transformed cells containing the vector plus RAPD-PCR product insert are identified by endonuclease digestion of minipreped DNA of isolated colonies. Minipreps of vector DNA containing the RAPD-PCR product are sequenced. Sequencing is performed on an ABI PRISM 377™ DNA sequencer (Applied Biosystems, Foster City, Calif.) using primers in the pCR4-TOPO cloning vector: FORWARD (5'-gtaaaacgacggccagt-3'; SEQ ID NO: 1) and REVERSE (5'-caggaaacagctatgac-3'; SEQ ID NO:2). Sequences obtained for each Tapesia spp. subtype are identified in Table 2.

TABLE 2

Tapesia spp. subtype-specific RAPD-PCR product sequences

| Sequence Identifier | Fungal Species | Subtype and Sequence ID | RAPD-PCR Sequence Length |
|---|---|---|---|
| SEQ-ID-NO: 3 | *Tapesia yallundae* | Ib1-27 | 525 |
| SEQ-ID-NO: 4 | *Tapesia yallundae* | Ib2-31 | 551 |
| SEQ-ID-NO: 5 | *Tapesia yallundae* | Ib3-33 | 520 |
| SEQ-ID-NO: 6 | *Tapesia yallundae* | Ic1-22 | 456 |
| SEQ-ID-NO: 7 | *Tapesia yallundae* | Ic 020502Ic4and6 | 711 |
| SEQ-ID-NO: 8 | *Tapesia yallundae* | Ic 020602D-20 | 555 |
| SEQ-ID-NO: 9 | *Tapesia yallundae* | Ic 020602D-21 | 625 |
| SEQ-ID-NO: 10 | *Tapesia acuformis* | IIp1-17 | 455 |
| SEQ-ID-NO: 11 | *Tapesia acuformis* | IIp 020602A-11 | 498 |
| SEQ-ID-NO: 12 | *Tapesia acuformis* | IIp 020602B-15 | 702 |

TABLE 2-continued

Tapesia spp. subtype-specific RAPD-PCR product sequences

| Sequence Identifier | Fungal Species | Subtype and Sequence ID | RAPD-PCR Sequence Length |
|---|---|---|---|
| SEQ-ID-NO: 13 | *Tapesia acuformis* | IIp 020602B-16 | 503 |
| SEQ-ID-NO: 14 | *Tapesia acuformis* | IIs2-39 | 513 |

Example 4

Design of Subtype-specific Primers

PCR Primers are designed to amplify within the sequences of RAPD-PCR products obtained according to Example 3. Primers are designed to be used either in conventional PCR reactions or with an oligonucleotide probe in TaqMan PCR reactions. Multiple primers are developed to target each RAPD-PCR *Tapesia* spp. subtype-specific sequence. These primers are listed in Table 3.

TABLE 3

Tapesia spp. subtype-specific primer sequences

| Sequence Identifier | Name | Species | Target DNA Subtype | RAPD-PCR Product | Oligo Sequence (5'-3') |
|---|---|---|---|---|---|
| SEQ-ID-NO: 15 | JB900 | *Tapesia yallundae* | Ib | Ib1-27/Ib2-31 | TGCGGTAGGGCGAAGAAAC |
| SEQ-ID-NO: 16 | JB901 | *Tapesia yallundae* | Ib | Ib1-27/Ib2-31 | CATCCTCCACCAACCAATACG |
| SEQ-ID-NO: 17 | JB902 Probe | *Tapesia yallundae* | Ib | Ib1-27/Ib2-31 | AACACCAAAGCGGCTTCGCGAGA |
| SEQ-ID-NO: 18 | JB903 | *Tapesia yallundae* | Ib | Ib1-27/Ib2-31 | CAGCCGATTGATCCGGTCTA |
| SEQ-ID-NO: 19 | JB904 | *Tapesia yallundae* | Ib | Ib1-27/Ib2-31 | GGCAACGCTGATTCGACTCTA |
| SEQ-ID-NO: 20 | JB905 | *Tapesia yallundae* | Ib | Ib1-27/Ib2-31 | GGTTCGATCCCGTCATCCT |
| SEQ-ID-NO: 21 | JB906 | *Tapesia yallundae* | Ib | Ib1-27/Ib2-31 | GTCGGTTCGATCCCGTCAT |
| SEQ-ID-NO: 22 | JB907 | *Tapesia yallundae* | Ib | Ib1-27/Ib2-31 | CAATACGCTCTGCGGTAGGGCGAA |
| SEQ-ID-NO: 23 | JB908 | *Tapesia yallundae* | Ib | Ib1-27/Ib2-31 | GCCGCTTTGGTGTTGGTTT |
| SEQ-ID-NO: 24 | JB909 | *Tapesia yallundae* | Ib | Ib1-27/Ib2-31 | CAGCCGATTGATCCGGTCTAT |
| SEQ-ID-NO: 25 | JB910 | *Tapesia yallundae* | Ib | Ib3-33 | AATTCGCCCTTGGACCTCTT |
| SEQ-ID-NO: 26 | JB911 | *Tapesia yallundae* | Ib | Ib3-33 | TTCGCCCTTGGACCTCTTG |
| SEQ-ID-NO: 27 | JB912 Probe | *Tapesia yallundae* | Ib | Ib3-33 | AGTAACACGCCCCACGGACGGAT |
| SEQ-ID-NO: 28 | JB913 | *Tapesia yallundae* | Ib | Ib3-33 | CTGCGGAGTCCTTGCTAGCT |
| SEQ-ID-NO: 29 | JB914 | *Tapesia yallundae* | Ib | Ib3-33 | GACCTGCGGAGTCCTTGCT |
| SEQ-ID-NO: 30 | JB915 | *Tapesia yallundae* | Ic | Ic1-22 | TTACACTGTATTTGTCTGGTGATTGC |
| SEQ-ID-NO: 31 | JB916 | *Tapesia yallundae* | Ic | Ic1-22 | GAGCCTCTCATATCTGGATCTCTAAATC |
| SEQ-ID-NO: 32 | JB917 Probe | *Tapesia yallundae* | Ic | Ic1-22 | TTAACTAGCAGTCATCTGTCCTGTGCCAAGG |
| SEQ-ID-NO: 33 | JB918 | *Tapesia yallundae* | Ic | Ic1-22 | GACAAACTCTACCAAGGAGAGACAAAA |
| SEQ-ID-NO: 34 | JB919 | *Tapesia yallundae* | Ic | Ic1-22 | CTACCAAGGAGAGACAAAACACAAAA |
| SEQ-ID-NO: 35 | JB920 | *Tapesia acuformis* | IIp | IIp1-17 | TCTTGTGAGACTGCATGGACTAGAGT |
| SEQ-ID-NO: 36 | JB921 | *Tapesia acuformis* | IIp | IIp1-17 | GATCTTGTGAGACTGCATGGACTAG |

TABLE 3-continued

Tapesia spp. subtype-specific primer sequences

| Sequence Identifier | Name | Species | Target DNA Subtype Product | RAPD-PCR Oligo | Sequence (5'-3') |
|---|---|---|---|---|---|
| SEQ-ID-NO: 37 | JB922 Probe | *Tapesia acuformis* | IIp | IIp1-17 | CATGCGAGAATTAAAGAGCTATAGTTGCGTGC |
| SEQ-ID-NO: 38 | JB923 | *Tapesia acuformis* | IIp | IIp1-17 | CGCAATCCTTTCTCGACTTCTAA |
| SEQ-ID-NO: 39 | JB924 | *Tapesia acuformis* | IIp | IIp1-17 | GTTTCGCAATCCTTTCTCGACTT |
| SEQ-ID-NO: 40 | JB925 | *Tapesia acuformis* | IIs | IIs2-39 | GCAGAATTCGCCCTTAAGTCG |
| SEQ-ID-NO: 41 | JB926 | *Tapesia acuformis* | IIs | IIs2-39 | TCTGCAGAATTCGCCCTTAAG |
| SEQ-ID-NO: 42 | JB927 Probe | *Tapesia acuformis* | IIs | IIs2-39 | AAGGTAGCCGTATCGGAAGGTGCGG |
| SEQ-ID-NO: 43 | JB928 | *Tapesia acuformis* | IIs | IIs2-39 | CCAGAACGGAGGTGATCCAG |
| SEQ-ID-NO: 44 | JB929 | *Tapesia acuformis* | IIs | IIs2-39 | TTCCAGAACGGAGGTGATCC |
| SEQ-ID-NO: 45 | JB930 | *Tapesia yallundae* | Ic | Ic1-22 | ATATTCTTGCTGAATTGGTC |
| SEQ-ID-NO: 46 | JB931 | *Tapesia yallundae* | Ic | Ic1-22 | CAAAATTATTTCATCCTTGGCACAG |
| SEQ-ID-NO: 47 | JB932 | *Tapesia yallundae* | Ic | Ic1-22 | AAATTATTTCATCCTTGGCACAGG |
| SEQ-ID-NO: 48 | JB933 | *Tapesia yallundae* | Ic | Ic1-22 | ATATTCTTGCTGAATTGGTC |
| SEQ-ID-NO: 49 | JB934 | *Tapesia acuformis* | IIp | IIp1-17 | AGATGGGCAGAGTGTAGATCTTGTG |
| SEQ-ID-NO: 50 | JB935 | *Tapesia acuformis* | IIp | IIp1-17 | GGAACCGAGAGAGTAGCAACAGAAC |
| SEQ-ID-NO: 51 | JB936 | *Tapesia acuformis* | IIp | IIp1-17 | CAGGAACCGAGAGAGTAGCAACAG |
| SEQ-ID-NO: 52 | JB937 | *Tapesia acuformis* | IIp | IIp1-17 | GCGTTCGGCTTGAAGTCATG |
| SEQ-ID-NO: 53 | JB938 | *Tapesia acuformis* | Ic | 0205021c4and6 | CCTTTGGTCGGGTGGGAGAA |
| SEQ-ID-NO: 54 | JB939 | *Tapesia acuformis* | Ic | 0205021c4and6 | GCCAGGCTGAATCTTGGGAA |
| SEQ-ID-NO: 55 | JB940 | *Tapesia acuformis* | Ic | 0205021c4and6 | CCAGGCTGAATCTTGGGAAA |
| SEQ-ID-NO: 56 | JB941 | *Tapesia acuformis* | Ic | 0205021c4and6 | CCAAGTACGCATCTCGGATG |
| SEQ-ID-NO: 57 | JB942 | *Tapesia acuformis* | Ic | 020602D-20 | GAAGTGTTTACTCTTTGCCG |
| SEQ-ID-NO: 58 | JB943 | *Tapesia acuformis* | Ic | 020602D-20 | AATATTGGTTCTTGATCCTG |
| SEQ-ID-NO: 59 | JB944 | *Tapesia acuformis* | Ic | 020602D-20 | TCGAGACAATAGAGATTTTC |
| SEQ-ID-NO: 60 | JB945 | *Tapesia acuformis* | Ic | 020602D-20 | GTGTGTCATTTTGGAAGATT |
| SEQ-ID-NO: 61 | JB946 | *Tapesia acuformis* | Ic | 020602D-21 | ACATACCATCTTGTAAATAGCC |
| SEQ-ID-NO: 62 | JB947 | *Tapesia acuformis* | Ic | 020602D-21 | CATAGTCAATCCAAGCTTTC |
| SEQ-ID-NO: 63 | JB948 | *Tapesia acuformis* | Ic | 020602D-21 | ATACCATCTTGTAAATAGCC |
| SEQ-ID-NO: 64 | JB949 | *Tapesia acuformis* | Ic | 020602D-21 | TATGCTTCTGGTCTTTGTTT |
| SEQ-ID-NO: 65 | JB950 | *Tapesia yallundae* | IIp | 020602A-11 | AATCAATGTCATGCGGTTCG |
| SEQ-ID-NO: 66 | JB951 | *Tapesia yallundae* | IIp | 020602A-11 | CACTTCCACGGCAGTGATAA |
| SEQ-ID-NO: 67 | JB952 | *Tapesia yallundae* | IIp | 020602A-11 | TTGTCTCTTGGGTAATCATG |
| SEQ-ID-NO: 68 | JB953 | *Tapesia yallundae* | IIp | 020602A-11 | GTGCCAAAAGGAACTGATTG |
| SEQ-ID-NO: 69 | JB954 | *Tapesia yallundae* | IIp | 020602B-16 | TGAGATTCCGGACTGCATTT |
| SEQ-ID-NO: 70 | JB955 | *Tapesia yallundae* | IIp | 020602B-16 | CAAACTGAGATTTCTCAACG |
| SEQ-ID-NO: 71 | JB956 | *Tapesia yallundae* | IIp | 020602B-15 | CCTTACCCGACCTGCCATGT |
| SEQ-ID-NO: 72 | JB957 | *Tapesia yallundae* | IIp | 020602B-15 | CTGGCGGCCATATCGACTTC |

TABLE 3-continued

Tapesia spp. subtype-specific primer sequences

| Sequence Identifier | Name | Species | Target DNA Subtype Product | RAPD-PCR Oligo | Sequence (5'-3') |
|---|---|---|---|---|---|
| SEQ-ID-NO: 73 | JB958 | *Tapesia yallundae* | IIp | 020602B-15 | ATTAGCAACTGGAATGCACA |
| SEQ-ID-NO: 74 | JB959 | *Tapesia yallundae* | IIp | 020602B-15 | AAGCCAGCTGCATGATGTTC |
| SEQ-ID-NO: 75 | JB960 | *Tapesia yallundae* | IIp | 020602B-16 | CGCCCTAGCACATCATCAAA |
| SEQ-ID-NO: 76 | JB961 | *Tapesia yallundae* | IIp | 020602B-16 | CCTAGCACATCATCAAAAGA |
| SEQ-ID-NO: 77 | JB962 | *Tapesia yallundae* | IIp | 020602B-16 | GGAGCATGGAAGCACTCGTA |

Example 5

Synthesis and Purification of Oligonucleotides

Oligonucleotides (primers) are synthesized by, for example, either Integrated DNA Technologies (Coralville, Iowa) or Midland Certified Reagent Company (Midland, Tex.). Primer sequences labeled as "probe" are synthesized with a fluorescent reporter group attached at the 5' end for example 6-carboxy-fluorescein or "FAM" and a fluorescence quenching group attached at the 3' end for example 6-carboxy-tetramethul-rhodamine or "TAMRA" or for example a dark quencher such as the proprietary Black Hole Quencher or "BHQ™" from Biosearch Technologies (Novato, Calif.).

Example 6

Polymerase Chain Reaction Amplification

Polymerase chain reactions are performed with the GeneAmp Kit from Perkin-Elmer (Foster City, Calif.; part no. N808-0009) using 50 mM KCl, 2.5 mM $MgCl_2$, 10 mM Tris-HCl, pH8.3, containing 200 μM of each dTTP, dATP, dCTP, and dGTP in 25 μL reactions containing 50 μM each primer, 0.25 U/μL of Taq polymerase and approximately 25 ng of genomic DNA per reaction. Reactions are run for 30–35 cycles of 15 s at 94° C., 15 s at 50° C.–70° C., and 45 s at 72° C. in a Perkin-Elmer Model 9600 or 9700 thermal cycler. The products are analyzed by loading 10 μl of each PCR sample on a 1.0% agarose gel and electrophoresing. The gel is stained with ethidium bromide and products are visualized under ultraviolet light.

Example 7

Determination of Primer Specificity to Purified Fungal Genomic DNA

PCRs are performed according to Example 6 using different primer combinations (Table 4) in an attempt to amplify single specific fragments. Specific PCR amplification products are produced from primers designed from RAPD-PCR product sequences of each *Tapesia* spp. subtype.

TABLE 4

Possible combinations of PCR primers for the specific amplification of Tapesia spp. subtypes Ic and IIp

| Target species subtype (RAPD-PCR Product) | Primer 1 | Sequence Identifier | Primer 2 | Sequence Identifier |
|---|---|---|---|---|
| *Tapesia yallundae* Ib (Ib1-27/Ib2-31) | JB900 | SEQ-ID-NO: 15 | JB903 | SEQ-ID-NO: 18 |
| *Tapesia yallundae* Ib (Ib1-27/Ib2-31) | JB900 | SEQ-ID-NO: 15 | JB904 | SEQ-ID-NO: 19 |
| *Tapesia yallundae* Ib (Ib1-27/Ib2-31) | JB901 | SEQ-ID-NO: 16 | JB903 | SEQ-ID-NO: 18 |
| *Tapesia yallundae* Ib (Ib1-27/Ib2-31) | JB901 | SEQ-ID-NO: 16 | JB904 | SEQ-ID-NO: 19 |
| *Tapesia yallundae* Ib (Ib1-27/Ib2-31) | JB905 | SEQ-ID-NO: 20 | JB908 | SEQ-ID-NO: 23 |
| *Tapesia yallundae* Ib (Ib1-27/Ib2-31) | JB905 | SEQ-ID-NO: 20 | JB909 | SEQ-ID-NO: 24 |
| *Tapesia yallundae* Ib (Ib1-27/Ib2-31) | JB906 | SEQ-ID-NO: 21 | JB908 | SEQ-ID-NO: 23 |
| *Tapesia yallundae* Ib (Ib1-27/Ib2-31) | JB906 | SEQ-ID-NO: 21 | JB909 | SEQ-ID-NO: 24 |
| *Tapesia yallundae* Ib (Ib3-33) | JB910 | SEQ-ID-NO: 25 | JB913 | SEQ-ID-NO: 28 |
| *Tapesia yallundae* Ib (Ib3-33) | JB910 | SEQ-ID-NO: 25 | JB914 | SEQ-ID-NO: 29 |
| *Tapesia yallundae* Ib (Ib3-33) | JB911 | SEQ-ID-NO: 26 | JB913 | SEQ-ID-NO: 28 |

TABLE 4-continued

Possible combinations of PCR primers for the specific amplification of Tapesia spp. subtypes Ic and IIp

| Target species subtype (RAPD-PCR Product) | Primer 1 | Sequence Identifier | Primer 2 | Sequence Identifier |
|---|---|---|---|---|
| *Tapesia yallundae* Ib (Ib3-33) | JB911 | SEQ-ID-NO: 26 | JB914 | SEQ-ID-NO: 29 |
| *Tapesia yallundae* Ic (1c1-22) | JB915 | SEQ-ID-NO: 30 | JB918 | SEQ-ID-NO: 33 |
| *Tapesia yallundae* Ic (1c1-22) | JB915 | SEQ-ID-NO: 30 | JB919 | SEQ-ID-NO: 34 |
| *Tapesia yallundae* Ic (1c1-22) | JB916 | SEQ-ID-NO: 31 | JB918 | SEQ-ID-NO: 33 |
| *Tapesia yallundae* Ic (1c1-22) | JB916 | SEQ-ID-NO: 31 | JB919 | SEQ-ID-NO: 34 |
| *Tapesia yallundae* Ic (1c1-22) | JB920 | SEQ-ID-NO: 35 | JB923 | SEQ-ID-NO: 38 |
| *Tapesia yallundae* Ic (Ic1-22) | JB920 | SEQ-ID-NO: 35 | JB924 | SEQ-ID-NO: 39 |
| *Tapesia yallundae* Ic (1c1-22) | JB921 | SEQ-ID-NO: 36 | JB923 | SEQ-ID-NO: 38 |
| *Tapesia yallundae* Ic (1c1-22) | JB921 | SEQ-ID-NO: 36 | JB924 | SEQ-ID-NO: 39 |
| *Tapesia acuformis* IIs (IIs2-39) | JB925 | SEQ-ID-NO: 40 | JB928 | SEQ-ID-NO: 43 |
| *Tapesia acuformis* IIs (IIs2-39) | J8925 | SEQ-ID-NO: 40 | JB929 | SEQ-ID-NO: 44 |
| *Tapesia acuformis* IIs (IIs2-39) | JB926 | SEQ-ID-NO: 41 | JB928 | SEQ-ID-NO: 43 |
| *Tapesia acuformis* IIs (IIs2-39) | JB926 | SEQ-ID-NO: 41 | JB929 | SEQ-ID-NO: 44 |
| *Tapesia yallundae* Ic (Ic1-22) | JB930 | SEQ-ID-NO: 45 | JB931 | SEQ-ID-NO: 46 |
| *Tapesia yallundae* Ic (Ic1-22) | JB930 | SEQ-ID-NO: 45 | JB932 | SEQ-ID-NO: 47 |
| *Tapesia yallundae* Ic (Ic1-22) | JB933 | SEQ-ID-NO: 48 | JB931 | SEQ-ID-NO: 46 |
| *Tapesia yallundae* Ic (Ic1-22) | JB933 | SEQ-ID-NO: 48 | JB932 | SEQ-ID-NO: 47 |
| *Tapesia acuformis* IIs/IIp (IIp1–17) | JB934 | SEQ-ID-NO: 49 | JB935 | SEQ-ID-NO: 50 |
| *Tapesia acuformis* IIp (IIp1–17) | JB934 | SEQ-ID-NO: 49 | JB936 | SEQ-ID-NO: 51 |
| *Tapesia acuformis* IIs/IIp (IIp1–17) | JB937 | SEQ-ID-NO: 52 | JB935 | SEQ-ID-NO: 50 |
| *Tapesia acuformis* IIp (IIp1–17) | JB937 | SEQ-ID-NO: 52 | JB936 | SEQ-ID-NO: 51 |
| *Tapesia yallundae* Ic (0205021c4and6) | JB938 | SEQ-ID-NO: 53 | JB939 | SEQ-ID-NO: 54 |
| *Tapesia yallundae* Ic (0205021c4and6) | JB938 | SEQ-ID-NO: 53 | JB940 | SEQ-ID-NO: 55 |
| *Tapesia yallundae* Ic (0205021c4and6) | JB941 | SEQ-ID-NO: 56 | JB939 | SEQ-ID-NO: 54 |
| *Tapesia yallundae* Ic (0205021c4and6) | JB941 | SEQ-ID-NO: 56 | JB940 | SEQ-ID-NO: 55 |
| *Tapesia yallundae* Ic (020602D-20) | JB942 | SEQ-ID-NO: 57 | JB943 | SEQ-ID-NO: 58 |
| *Tapesia yallundae* Ic (020602D-20) | JB942 | SEQ-ID-NO: 57 | JB945 | SEQ-ID-NO: 60 |
| *Tapesia yallundae* Ic (020602D-20) | JB944 | SEQ-ID-NO: 59 | JB943 | SEQ-ID-NO: 58 |
| *Tapesia yallundae* Ic (020602D-20) | JB944 | SEQ-ID-NO: 59 | JB945 | SEQ-ID-NO: 60 |
| *Tapesia yallundae* Ic (020602D-21) | JB946 | SEQ-ID-NO: 61 | JB947 | SEQ-ID-NO: 62 |
| *Tapesia yallundae* Ic (020602D-21) | JB946 | SEQ-ID-NO: 61 | JB949 | SEQ-ID-NO: 64 |
| *Tapesia yallundae* Ic (020602D-21) | JB948 | SEQ-ID-NO: 63 | JB947 | SEQ-ID-NO: 62 |
| *Tapesia yallundae* Ic (020602D-21) | JB948 | SEQ-ID-NO: 63 | JB949 | SEQ-ID-NO: 64 |
| *Tapesia acuformis* IIp (020602A-11) | JB952 | SEQ-ID-NO: 67 | JB950 | SEQ-ID-NO: 65 |
| *Tapesia acuformis* IIp (020602A-11) | JB952 | SEQ-ID-NO: 67 | JB951 | SEQ-ID-NO: 66 |
| *Tapesia acuformis* IIp (020602A-11) | JB953 | SEQ-ID-NO: 68 | JB950 | SEQ-ID-NO: 65 |
| *Tapesia acuformis* IIp (020602A-11) | JB953 | SEQ-ID-NO: 68 | JB9SI | SEQ-ID-NO: 66 |
| *Tapesia acuformis* IIp (020602B-16) | JB954 | SEQ-ID-NO: 69 | JB955 | SEQ-ID-NO: 70 |
| *Tapesia acuformis* IIp (020602B-16) | JB954 | SEQ-ID-NO: 69 | JB960 | SEQ-ID-NO: 75 |
| *Tapesia acuformis* IIp (020602B-16) | JB954 | SEQ-ID-NO: 69 | JB961 | SEQ-ID-NO: 76 |
| *Tapesia acuformis* IIp (020602B-16) | JB962 | SEQ-ID-NO: 77 | JB955 | SEQ-ID-NO: 70 |
| *Tapesia acuformis* IIp (020602B-16) | JB962 | SEQ-ID-NO: 77 | JB960 | SEQ-ID-NO: 75 |
| *Tapesia acuformis* IIp (020602B-16) | JB962 | SEQ-ID-NO: 77 | JB961 | SEQ-ID-NO: 76 |
| *Tapesia acuformis* IIp (020602B-15) | JB956 | SEQ-ID-NO: 71 | JB957 | SEQ-ID-NO: 72 |
| *Tapesia acuformis* IIp (020602B-15) | JB956 | SEQ-ID-NO: 71 | JB959 | SEQ-ID-NO: 74 |
| *Tapesia acuformis* IIp (020602B-15) | JB958 | SEQ-ID-NO: 73 | JB957 | SEQ-ID-NO: 72 |
| *Tapesia acuformis* IIp (020602B-15) | JB958 | SEQ-ID-NO: 73 | JB959 | SEQ-ID-NO: 74 |

In an initial screen for specificity, PCR reaction mixtures are made according to Example 6 for each of the primer combinations in Table 4. These are run against a negative control (no DNA added) and approximately 25 ng of fungal DNA for each of the *Tapesia* spp. subtypes listed in Table 1 prepared as described in example 1.

When visualized on an ethidium bromide stained gel several primer pairs give satisfactory results: good amplification of target DNA from multiple isolates of the target species subtype with all other reactions (negative control and other fungal DNAs) free of both specific and nonspecific reaction products. Some give unsatisfactory results including nonspecific amplification, no amplification of target DNA, and amplification of DNAs from fungal species other that the target. The primer pairs that give good specific amplification for *T. yallundae* subtype Ic target DNA with no cross-amplification are summarized in Table 5.

TABLE 5

PCR primer pairs providing specific and sensitive amplification of target DNAs for *Tapesia yallundae* subtype Ic.

| Target species subtype (RAPD-PCR Product) | Primer 1 | Sequence Identifier | Primer 2 | Sequence Identifier |
|---|---|---|---|---|
| *Tapesia yallundae* Ic (020602D-20) | JB944 | SEQ-ID-NO: 59 | JB943 | SEQ-ID-NO: 58 |
| *Tapesia yallundae* Ic (020602D-20) | JB944 | SEQ-ID-NO: 59 | JB945 | SEQ-ID-NO: 60 |

When primers JB944 and JB943 or primers JB944 and JB945 are run against DNA preparations of the eyespot subtypes listed in Table 1 the following results are recorded (Table 6).

TABLE 6

Results of primer pairs JB944 and JB943 and JB944 and JB945 on test isolates of Tapesia spp.

| Fungal | Fungal | Subtype | PCR Results (+/−) | |
|---|---|---|---|---|
| Species | Isolate | Identifier | JB944/JB943 | JB944/JB945 |
| *Tapesia yallundae* | 627 N | Ia | − | − |
| *Tapesia yallundae* | 646 N | Ib | − | − |
| *Tapesia yallundae* | 572 N | Ic | + | + |
| *Tapesia yallundae* | 618 N | Ic | + | + |
| *Tapesia acuformis* | 634 L | Iis | − | − |
| *Tapesia acuformis* | 643 L | Iis | − | − |
| *Tapesia acuformis* | 567 L | Iip | − | − |
| *Tapesia acuformis* | 617 L | Iip | − | − |
| *Tapesia acuformis* | 626 L | Iip | − | − |

Thus, primer pairs JB944 and JB943 and primers JB944 and JB945 are useful in the differentiation of subtypes within the *Tapesia yallundae* species.

For specificity to *T. acuformis* subtypes IIs and IIp primer pairs were selected that amplify from both *T. acuformis* subtypes but with different sized PCR products that allow differentiation of the subtype by product size. Again, primers were selected based on good amplification of target DNA from multiple isolates of the target species subtype with all other reactions (negative control and other fungal DNAs) free of both specific and nonspecific reaction products. Some give unsatisfactory results including nonspecific amplification, no amplification of target DNA, and amplification of DNAs from fungal species other that the target. The primer pairs that give good specific amplification for *T. acuformis* subtypes IIs and IIp with different sized products for each subtype with no cross-amplification are summarized in Table 7.

TABLE 7

PCR primer pairs providing specific and sensitive amplification of target DNAs for *Tapesia acuformis* subtypes IIs and IIp.

| Target species subtype (RAPD-PCR Product) | Primer 1 | Sequence Identifier | Primer 2 | Sequence Identifier |
|---|---|---|---|---|
| *Tapesia acuformis* IIs/IIp (IIp1–17) | JB934 | SEQ-ID-NO: 49 | JB935 | SEQ-ID-NO: 50 |
| *Tapesia acuformis* IIs/IIp (IIp1–17) | JB937 | SEQ-ID-NO: 52 | JB935 | SEQ-ID-NO: 50 |

Primers JB934 and JB935 are run against DNA preparations of the eyespot subtypes listed in Table 1. The results are presented in Table 8).

TABLE 8

Results of primer pairs JB934 and JB935 on test isolates of Tapesia spp.

| Fungal Species | Fungal Isolate | Subtype Identifier | PCR Results (+/−) (+/−) | PCR Results (+/−) Amplification Product Size |
|---|---|---|---|---|
| *Tapesia yallundae* | 627 N | Ia | − | − |
| *Tapesia yallundae* | 646 N | Ib | − | − |
| *Tapesia yallundae* | 572 N | Ic | − | − |
| *Tapesia yallundae* | 618 N | Ic | − | − |
| *Tapesia acuformis* | 634 L | IIs | + | ~600 |
| *Tapesia acuformis* | 643 L | IIs | + | ~600 |
| *Tapesia acuformis* | 567 L | IIp | + | ~400 |
| *Tapesia acuformis* | 617 L | IIp | + | ~400 |
| *Tapesia acuformis* | 626 L | IIp | + | ~400 |

Thus, primer pairs JB934 and JB935 are specific to *Tapesia acuformis* at the species level and provide differently sized PCR products that are useful in the differentiation of IIs and IIp subtypes within the *Tapesia acuformis* species.

Example 8

TaqMan Based Detection of *Tapesia* spp. Subtypes

Some of the primers detailed in Table in 3 were designed for the additional possible use in TaqMan reactions for detection of specific *Tapesia* spp. subtypes. Possible primer combinations for these reactions are listed in Table 9.

TABLE 9

Possible combinations of TaqMan primers and probes for the specific amplification of Tapesia spp. subtypes

| Target species subtype (RAPD-PCR Product) | Primer 1 | Sequence Identifier | Probe | Sequence Identifier | Primer 2 | Sequence Identifier |
|---|---|---|---|---|---|---|
| *Tapesia yallundae* Ib (Ib1–27/Ib2–31) | JB900 | SEQ-ID-NO: 15 | JB902 | SEQ-ID-NO: 17 | JB903 | SEQ-ID-NO: 18 |
| *Tapesia yallundae* Ib (Ib1–27/Ib2–31) | JB900 | SEQ-ID-NO: 15 | JB902 | SEQ-ID-NO: 17 | JB904 | SEQ-ID-NO: 19 |
| *Tapesia yallundae* Ib (Ib1–27/Ib2–31) | JB901 | SEQ-ID-NO: 16 | JB902 | SEQ-ID-NO: 17 | JB903 | SEQ-ID-NO: 18 |
| *Tapesia yallundae* Ib (Ib1–27/Ib2–31) | JB901 | SEQ-ID-NO: 16 | JB902 | SEQ-ID-NO: 17 | JB904 | SEQ-ID-NO: 19 |
| *Tapesia yallundae* Ib (Ib1–27/Ib2–31) | JB905 | SEQ-ID-NO: 20 | JB907 | SEQ-ID-NO: 22 | JB908 | SEQ-ID-NO: 23 |
| *Tapesia yallundae* Ib (Ib1–27/Ib2–31) | JB905 | SEQ-ID-NO: 20 | JB907 | SEQ-ID-NO: 22 | JB909 | SEQ-ID-NO: 24 |
| *Tapesia yallundae* Ib (Ib1–27/Ib2–31) | JB906 | SEQ-ID-NO: 21 | JB907 | SEQ-ID-NO: 22 | JB908 | SEQ-ID-NO: 23 |
| *Tapesia yallundae* Ib (Ib1–27/Ib2–31) | JB906 | SEQ-ID-NO: 21 | JB907 | SEQ-ID-NO: 22 | JB909 | SEQ-ID-NO: 24 |
| *Tapesia yallundae* Ib (Ib3–33) | JB910 | SEQ-ID-NO: 25 | JB912 | SEQ-ID-NO: 27 | JB913 | SEQ-ID-NO: 28 |
| *Tapesia yallundae* Ib (Ib3–33) | JB910 | SEQ-ID-NO: 25 | JB912 | SEQ-ID-NO: 27 | JB914 | SEQ-ID-NO: 29 |
| *Tapesia yallundae* Ib (Ib3–33) | JB911 | SEQ-ID-NO: 26 | JB912 | SEQ-ID-NO: 27 | JB913 | SEQ-ID-NO: 28 |
| *Tapesia yallundae* Ib (Ib3–33) | JB911 | SEQ-ID-NO: 26 | JB912 | SEQ-ID-NO: 27 | JB914 | SEQ-ID-NO: 29 |
| *Tapesia yallundae* Ic (lc1–22) | JB915 | SEQ-ID-NO: 30 | JB917 | SEQ-ID-NO: 32 | JB918 | SEQ-ID-NO: 33 |
| *Tapesia yallundae* Ic (lc1–22) | JB915 | SEQ-ID-NO: 30 | JB917 | SEQ-ID-NO: 32 | JB919 | SEQ-ID-NO: 34 |
| *Tapesia yallundae* Ic (lc1–22) | JB916 | SEQ-ID-NO: 31 | JB917 | SEQ-ID-NO: 32 | JB918 | SEQ-ID-NO: 33 |
| *Tapesia yallundae* Ic (lc1–22) | JB916 | SEQ-ID-NO: 31 | JB917 | SEQ-ID-NO: 32 | JB919 | SEQ-ID-NO: 34 |
| *Tapesia yallundae* Ic (lc1–22) | JB920 | SEQ-ID-NO: 35 | JB922 | SEQ-ID-NO: 37 | JB923 | SEQ-ID-NO: 38 |
| *Tapesia yallundae* Ic (lc1–22) | JB920 | SEQ-ID-NO: 35 | JB922 | SEQ-ID-NO: 37 | JB924 | SEQ-ID-NO: 39 |
| *Tapesia yallundae* Ic (lc1–22) | JB921 | SEQ-ID-NO: 36 | JB922 | SEQ-ID-NO: 37 | JB923 | SEQ-ID-NO: 38 |
| *Tapesia yallundae* Ic (lc1–22) | JB921 | SEQ-ID-NO: 36 | JB922 | SEQ-ID-NO: 37 | JB924 | SEQ-ID-NO: 39 |
| *Tapesia acuformis* IIs (IIs2–39) | JB925 | SEQ-ID-NO: 40 | JB927 | SEQ-ID-NO: 42 | JB928 | SEQ-ID-NO: 43 |
| *Tapesia acuformis* IIs (IIs2–39) | JB925 | SEQ-ID-NO: 40 | JB927 | SEQ-ID-NO: 42 | JB929 | SEQ-ID-NO: 44 |
| *Tapesia acuformis* IIs (IIs2–39) | JB926 | SEQ-ID-NO: 41 | JB927 | SEQ-ID-NO: 42 | JB928 | SEQ-ID-NO: 43 |
| *Tapesia acuformis* IIs (IIs2–39) | JB926 | SEQ-ID-NO: 41 | JB927 | SEQ-ID-NO: 42 | JB929 | SEQ-ID-NO: 44 |

The combinations listed in Table 7 are tested in initial TaqMan™ screens for subtype level specificity. Primer and probe combinations are tested for their ability to amplify from the target subtypes's DNA. Reaction conditions are held constant (1× TaqMan™ Universal Master Mix (Perkin Elmer, Norwalk, Conn.; part no. N430-4447), 300 nM each primer, 200 nM probe, approximately 25 ng pre reaction of fungal target genomic DNA, thermal cycling: 50° C. for 2 min., 95° C. for 10 min., 40 cycles of 95° C. for 15 s, 60° C. for 60 s). In initial screens for specificity under these conditions no primer/probe combination provides absolute specificity. It is prophetic that further experimentation with reaction conditions will provide subtype specific tests using these primers that are designed for specificity.

This invention also provides the possibility of assessing potential damage in a specific crop variety-pathogen strain relationship and of utilizing judiciously the diverse armory of fungicides which is available. Furthermore, it can be used to provide detailed information on the development and spread of specific pathogen races over extended geographical areas.

Kits useful in the practice of the invention are also provided. The kits find particular use in the identification of *Tapesia* pathogens.

While the present invention has been described with reference to specific embodiments thereof, it will be appreciated that numerous variations, modifications, and further embodiments are possible, and accordingly, all such variations, modifications and embodiments are to be regarded as being within the scope of the present invention.

Numerous patents, applications and references are discussed or cited within this specification, and all are incorporated by reference in their entireties.

What is claimed is:

1. An isolated nucleic acid molecule comprising the nucleic acid sequence of SEQ ID NO: 8.

2. A pair of oligonucleotide primers wherein at least one primer consists of the nucleotide sequence of SEQ ID NO: 58 or SEQ ID NO: 59.

3. A pair of oligonucleotide primers comprising:

JB944 (SEQ ID NO: 59) and JB943 (SEQ ID NO: 58).

4. A method for the detection of a fungal pathogen, comprising the steps of:

(a) isolating DNA from a plant tissue infected with a pathogen;

(b) subjecting said DNA to polymerase chain reaction amplification using at least one primer that comprises the sequence of SEQ ID NO: 58 or SEQ ID NO:59 and (c) detecting said fungal pathogen by visualizing the product or products of said polymerase chain reaction amplification.

5. The method of claim 4, wherein the fungal pathogen is *Tapesia yallundae, Tapesia acuformis.*

6. The method of claim 5, wherein the *Tapesia yallundae* is subtype Ic., *Tapesia acuformis* subtypes IIs or IIp.

7. A diagnostic kit used in detecting a fungal pathogen having at least one primer that comprises SEQ ID NO: 58 or SEQ ID NO: 59.

8. The diagnostic kit of claim 7, wherein the pair of primers are JB944 (SEQ ID NO: 59) and JB943 (SEQ ID NO: 58).

* * * * *

SEQUENCE LISTING

```
<160> NUMBER OF SEQ ID NOS: 77

<210> SEQ ID NO 1
<211> LENGTH: 17
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(17)

<400> SEQUENCE: 1

gtaaaacgac ggccagt                                                 17
```

-continued

<210> SEQ ID NO 2
<211> LENGTH: 17
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(17)

<400> SEQUENCE: 2
caggaaacag ctatgac 17

<210> SEQ ID NO 3
<211> LENGTH: 525
<212> TYPE: DNA
<213> ORGANISM: Tapesia yallundae

<400> SEQUENCE: 3
tgggccctct agatgcatgc tcgagcggcc gccagtgtga tggatatctg cagaattcgc 60
ccttaagtcg taacaaggta gccgtatcgg aaggtgcggc tggatcacct cctttctgga 120
aaacagcatt caatattgaa cgcccacact tatcggttgt tggaagaagt cggtgctaac 180
cgacatgggt ctgtagctca gctggttaga gcaccgtctt gataaggcgg gggtcgttgg 240
ttcgagccca actagaccca ccaaatcttc cgaacataag atgcgaggat cagtggggga 300
ttagctcagc tgggagagca cctgctttgc aagcaggggg tcgtcggttc gatcccgtca 360
tcctccacca accaatacgc tctgcggtag ggcgaagaaa ccaacaccaa agcggcttcg 420
cgagaggcct ctttgttgtt ggtccggtat agaccggatc aatcggctgt tctttaaaaa 480
ttcatagagt cgaatcagcg ttgccggcgg aaagcaggaa actgc 525

<210> SEQ ID NO 4
<211> LENGTH: 551
<212> TYPE: DNA
<213> ORGANISM: Tapesia yallundae

<400> SEQUENCE: 4
gggccctcta gatgcatgct cgagcggccg ccagtgtgat ggatatctgc agaattcgcc 60
cttaagtcgt aacaaggtag ccgtatcgga aggtgcggct ggatcacctc ctttctggaa 120
aacagcattc aatattgaac gcccacactt atcggttgtt ggaagaagtc ggtgctaacc 180
gacatgggtc tgtagctcag ctggttagag caccgtcttg ataaggcggg ggtcgttggt 240
tcgagcccaa ctagacccac caaatcttcc gaacataaga tgcgaggatc agtgggggat 300
tagctcagct gggagagcac ctgctttgca agcagggggt cgtcggttcg atcccgtcat 360
cctccaccaa ccaatacgct ctgcggtagg gcgaagaaac caacaccaaa gcggcttcgc 420
gagaggcctc tttgttgttg gtccggtata gaccggatca atcggctgtt ctttaaaaat 480
tcatagagtc gaatcagcgt tgcccggcgg aaagcaggaa actgcacccg tgccgccggt 540
gacaaaaatt t 551

<210> SEQ ID NO 5
<211> LENGTH: 520
<212> TYPE: DNA
<213> ORGANISM: Tapesia yallundae

<400> SEQUENCE: 5
gggccctcta gatgcatgct cgagcggccg ccagtgtgat ggatatctgc agaattcgcc 60
cttggacctc ttggagtaac acgccccacg gacggatcag ctagcaagga ctccgcaggt 120

-continued ctacttgtag taagccctgg tatggactcg gcattttaca aagtaaattc tcatgaaata 180
tgttttgggc tcggctaatg attgtagggc tttggtctca acattagtaa cgagctggta 240
aaagtgaagg cgcgaatgct acctgcaccg accctgttgt tcaagggcaa taagccagat 300
aaggtgcagg atagcttggg actggggtac aagggaacgt ggaacctatc agatatcaca 360
ttttactcgc ccggtaggcc atctgacgaa accgaatacc tcgaactagg gttcatcaag 420
atgggaaacg tctccgacac ggacatagac acatttgcaa accagcttca tctagacctg 480
aacaagtatg gtatcacacc caatcacaac aagaaggaca 520

<210> SEQ ID NO 6
<211> LENGTH: 456
<212> TYPE: DNA
<213> ORGANISM: Talesia yallundae

<400> SEQUENCE: 6
ttcgcccttt ggtcgggtgc aaatatgtat ttagaattgt tatatattct tgctgaattg 60
gtctctttaa tattatataa cgactttctt agtccttttt ttttttaac tgtttttaga 120 tggtttttc tcttgccatt tttaggattc actcttcact ttgacttcag acagtctgat 180
tataatgttg ccatggtgga gaccttttta cactgtattt gtctggtgat tgctgagcct 240
ctcatatctg gatctctaaa tctcttaact agcagtcatc tgtcctgtgc caaggatgaa 300
ataattttgt gttttgtctc tccttggtag agtttgtcac ccccaagtaa gaactaaggc 360
tctgagaaaa taagttttgc ccaacctaag tgtagtatgt tcaagtcaga tatttaaacc 420
taatccaaca tttcttgccc caaccatctc tataag 456

<210> SEQ ID NO 7
<211> LENGTH: 711
<212> TYPE: DNA
<213> ORGANISM: Tapesia yallundae

<400> SEQUENCE: 7
ctaaagggac tagtcctgca ggtttaaacg aattcgccct ttggtcgggt gggagaacct 60
tcgtgctgag attacagaac gatcggaaaa ccaagtacgc atctcggatg tagacttcgt 120
cctcgctgtc ctcggaatcc atgccttcgt ctattgtact ctccgggggc gtttcccctt 180
ccgcatatcg aggggagggt tgtgggttct tcagctgtgt aaccatggtt gatccatctc 240
ccatttgcga atcgtcgaag ctctttcgat gttcgaggtc cttgagcgta agttttggcc 300
catcattgtc ggattggact tcagaggcca cactttcctc cacggcttct tccacctcgg 360
tgtccccatt ggcgtcgggc gatgcatcga ccgtgaaaga actagtattt cccccgttct 420
tctcgagttt cccaagattc agcctggcct ctttcatgtg tattcgtgtc ttgacccttt 480
cgaacactgt cccaaccatc tgtgtcaaag tcccctgcgc aacctgctgg ttcgcactgc 540
ttttcgaaag aaggaacaca ttgtagacct gcctgactgc cttcaatagt ccagcgccgt 600
gtaccacaat tttgtcattc agcacagctg cgagtaacga ctttacaatc tgtaactgga 660
tttccaccgg cgtagtctcc ccctgaaagc agtcgcatat tgtattgata g 711

<210> SEQ ID NO 8
<211> LENGTH: 555
<212> TYPE: DNA
<213> ORGANISM: Tapesia yallundae

<400> SEQUENCE: 8

-continued

```
gtgcgagacg atgcgatcgt cgatcagaga agtgtttact ctttgccgaa gctataacag     60

gacaacagtg aggaagtgta ctcgagtcga gacaatagag attttcaacg aagaacttaa    120

gctccaacag cagaggggct ttcttttgat ctgcctgaag atggacagcc tcatgttggg    180

ccgaattcat cgtcagacta cacagccttg ctgcccaatt gacgcccggc tgctgagcat    240

cacgtgttac cacttttcca gctcagctca gcttagtctg atcttcttcc atttcaagtc    300

aagacaatct tcgaggtccg tggcaaaact gatttcgata ctttcttctg ttggatatcc    360

atctttgtac tcgggggcag gatcaagaac caatattcca acccgacgag tgatcccatc    420

tcgtgtctca agtactaggc cgtgtcgcga gctagcccaa tcttccaaaa tgacacactc    480

aaacaaatct tgatcgaaaa cttccgacct ctggtcagtc ttacggtctt gtcggttgtc    540

ggggtagaat agaca                                                      555
```

<210> SEQ ID NO 9
<211> LENGTH: 625
<212> TYPE: DNA
<213> ORGANISM: Tapesia yallundae

<400> SEQUENCE: 9

```
caagggaatg atacacgtga ctgggtctgg atgagtccaa aaatagaaga acataccatc     60

ttgtaaatag cctcaacaat agccagcatc tcgtcgtagc tgatctttcc gtctccatcg    120

atatcataga gttggaaggc ccagtctagt ttgtcctcca tcttccccct gctggtgacg    180

ctcaatgcgc agataaattc cttgaaatcg attgagcctg atttgtcgct atcgaataca    240

ttgaagacgt aatctgcgaa tgatgatgga tctccgaacg ggaagaattg gcggtaaatc    300

ttctggaact cctccttggt aagcatgccc gaaggacagt ccttcaagaa gcctggtcat    360

attagcttat gtttgagaaa agaccaggaa gtccataccc ttgtaccatt gttgcaactc    420

cttcttgtca aagtgtgttg atcgctgcaa ttcgctgagt tgctcttgcg aaagcttgga    480

ttgactatga agtaaaatta acttatagtc cgaaacaaag accagaagca taggaataga    540

agcccttacg attttcccat cttgaagttc tggttatgtg gttgaggagg gttgcgtatt    600

ctatcgtagc agagagggag actcg                                           625
```

<210> SEQ ID NO 10
<211> LENGTH: 455
<212> TYPE: DNA
<213> ORGANISM: Tapesia acuformis

<400> SEQUENCE: 10

```
cgcgaattcg cccttagatg ggcagagtgt agatcttgtg agactgcatg gactagagtg     60

ctgggaagtg atgtttttgt aagaggtgcg ttcggcttga agtcatgcga gaattaaaga    120

gctatagttg cgtgcaatta gaagtcgaga aaggattgcg aaacttcaat atgacaatcg    180

cccattcaaa agctatcaaa gagtgtgaga tattctagga tatctttttt taaataagtg    240

aaggctcgtc ggctagcaaa actagctcgc ctcgactttt gttcaaattc attgtcacga    300

atgtacgtgc cttagttgcc tgcagaactt ctcctttaga tgtttttaca ttgaatgcct    360

catcataact cgaatgatat cgaaagttct ctctgaaatg atagtaatct gtgtagtgtt    420

ctgttgctac tctctcggtt cctgaagatg tgctc                                455
```

<210> SEQ ID NO 11
<211> LENGTH: 498
<212> TYPE: DNA
<213> ORGANISM: Tapesia acuformis -continued

<400> SEQUENCE: 11

```
ctcaccaatt tcaggaaatt atttcattgc attctttttg tctcttgggt aatcatgcaa     60
gtagttcttt ccatgcttga caaatcgata agattacagg tgaacccccca gagtagtgcc   120
aaaaggaact gattgactgt gattgtcaac aaccctatat tcaggaatat ttcctaactt    180
gaagctgccc attctctccg tccgtgcgta gtcattcatc ctccgatcct caaaacttca    240
ccaccgattc atcaacccat gtttaatcat aaatttctgg agctgtcaag cttcactttg    300
acaggtttca actggctcat cctatccggc ttcgcttcgc ttgagtgact ggctggacct    360
gccggattgg gacctagagc acgtactgga tccctgacta cgacttatca ctgccgtgga    420
agtgggatgg agatacaaac gggcggcgaa ccgcatgaca ttgattagtt gattgaatat    480
atatatcata cattcact                                                 498
```

<210> SEQ ID NO 12
<211> LENGTH: 702
<212> TYPE: DNA
<213> ORGANISM: Tapesia acuformis

<400> SEQUENCE: 12

```
aagggactag tcctgcaggt ttaaacgaat tcgcccttac ccgacctgcc atgtgaccat     60
gtaatgcttg aagtgtcctc caactgccat cttaaactcg tacaaatcgt caaccattag    120
caactggaat gcacaactcg agattgcaat caagctctct ctcttacccc caattaccaa    180
ccatgttttc accgagataa gagtgtcctc cgggtccaga atgaatccca gtccattcaa    240
catcctgcaa gccttctcat cacctcaaag gagtcaccct cttccatctc aaggctggag    300
aaagtctcat gatcgtagat ttggcagcct tcaaatatca tccgaacatt gtccaagggt    360
gtagaaagat attccgcagc caccttccgg agtctaccaa actcggtttg aggcccgatg    420
cggaagtcga tatggccgcc agtagataac cttgccgtga cgatgacttg acgtgaaccg    480
gcagtgcctt gactgatggg aacatcatgc agctggcttg cgggtggagc aagtgcacga    540
ggtgctttga taggatgggt cagaaagaac gacttgtaaa tgccctccat cgcagcgagt    600
ctcttgcttc tcgattccgc ctcctcgtgg ctggctccct caggtcgggt aagggcgaat    660
tcgcggccgc taaattcaat tcgccctata gtgagtcgta tt                       702
```

<210> SEQ ID NO 13
<211> LENGTH: 503
<212> TYPE: DNA
<213> ORGANISM: Tapesia acuformis

<400> SEQUENCE: 13

```
tatagggcga attgaattta gcggccgcga attcgccctt acccgacctg agattccgga     60
ctgcattttg tttggtgttg atgattttcg cgtacttgac gaagatggat tacccagaaa    120
gagggacaga gatattcaga ggagcatgga agcactcgta aagctcagga tcatatgctg    180
gcggggtaaa ataggcttgg cacggcggag cgaggggcag tgaggttccg ccagcaagaa    240
gtccttaagc aatgtctata agtaccgtta tactatttgt cgcatcctaa gagtatcata    300
actcgaataa agtaaagtaa agtcctgcat cgtttcaaga ctttgatatc atttcatgcg    360
ttgagaaatc tcagtttgcc catcttttga tgatgtgcta gggcggagct ccactccact    420
caagctctcc cgcgcaggtc gggtaagggc gaattcgttt aaacctgcag gactagtccc    480
tttaggaggg ttaattctga gct                                            503
```

-continued

<210> SEQ ID NO 14
<211> LENGTH: 513
<212> TYPE: DNA
<213> ORGANISM: Tapesia acuformis

<400> SEQUENCE: 14
tgggccctct agatgcatgc tcgagcggcc gccagtgtga tggatatctg cagaattcgc 60
ccttaagtcg taacaaggta gccgtatcgg aaggtgcggc tggatcacct ccgttctgga 120
aaactgcatt caatattgaa cgcccacact tatcggttgt tggaagagtc ggtctgaccg 180
acatgggtct gtagctcagc tggttagagc accgtcttga taaggcgggg gtcgttggtt 240
cgagcccaac tagacccacc aaatcttcca aacatcagat gcgaggatca ttgggggatt 300
agctcagctg ggagagcacc tgctttgcaa gcagggggtc gtcggttcga tcccgtcatc 360
ctccaccaac caatcggtat caatgcaaca ccaaagaggc tttgaaaaag gcttctttgt 420
tgttgatcga gattactcag atcaatcggc tgttctttaa aaattcatag agtcgaatca 480
gcgttgctga tggaaactgc acattcgtaa agg 513

<210> SEQ ID NO 15
<211> LENGTH: 19
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(19)

<400> SEQUENCE: 15
tgcggtaggg cgaagaaac 19

<210> SEQ ID NO 16
<211> LENGTH: 21
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(21)

<400> SEQUENCE: 16
catcctccac caaccaatac g 21

<210> SEQ ID NO 17
<211> LENGTH: 23
<212> TYPE: DNA
<213> ORGANISM: artificial sequence
<220> FEATURE:
<223> OTHER INFORMATION: probe
<220> FEATURE:
<221> NAME/KEY: misc_feature
<222> LOCATION: (1)..(23)

<400> SEQUENCE: 17
aacaccaaag cggcttcgcg aga 23

<210> SEQ ID NO 18
<211> LENGTH: 20
<212> TYPE: DNA
<213> ORGANISM: artificial sequence
<220> FEATURE:
<223> OTHER INFORMATION: primer
<220> FEATURE:

-continued

<221> NAME/KEY: misc_feature
<222> LOCATION: (1)..(20)

<400> SEQUENCE: 18
cagccgattg atccggtcta 20

<210> SEQ ID NO 19
<211> LENGTH: 21
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(21)

<400> SEQUENCE: 19
ggcaacgctg attcgactct a 21

<210> SEQ ID NO 20
<211> LENGTH: 19
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(19)

<400> SEQUENCE: 20
ggttcgatcc cgtcatcct 19

<210> SEQ ID NO 21
<211> LENGTH: 19
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(19)

<400> SEQUENCE: 21
ggttcgatcc cgtcatcct 19

<210> SEQ ID NO 22
<211> LENGTH: 24
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(24)

<400> SEQUENCE: 22
caatacgctc tgcggtaggg cgaa 24

<210> SEQ ID NO 23
<211> LENGTH: 19
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(19)

<400> SEQUENCE: 23

-continued gccgctttgg tgttggttt 19

<210> SEQ ID NO 24
<211> LENGTH: 21
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(21)

<400> SEQUENCE: 24
cagccgattg atccggtcta t 21

<210> SEQ ID NO 25
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 25
aattcgccct tggacctctt 20

<210> SEQ ID NO 26
<211> LENGTH: 19
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(19)

<400> SEQUENCE: 26
ttcgcccttg gacctcttg 19

<210> SEQ ID NO 27
<211> LENGTH: 23
<212> TYPE: DNA
<213> ORGANISM: artificial sequence
<220> FEATURE:
<223> OTHER INFORMATION: probe
<220> FEATURE:
<221> NAME/KEY: misc_feature
<222> LOCATION: (1)..(23)

<400> SEQUENCE: 27
agtaacacgc cccacggacg gat 23

<210> SEQ ID NO 28
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 28
ctgcggagtc cttgctagct 20

-continued

<210> SEQ ID NO 29
<211> LENGTH: 19
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(19)

<400> SEQUENCE: 29
gacctgcgga gtccttgct 19

<210> SEQ ID NO 30
<211> LENGTH: 26
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(26)

<400> SEQUENCE: 30
ttacactgta tttgtctggt gattgc 26

<210> SEQ ID NO 31
<211> LENGTH: 28
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(28)

<400> SEQUENCE: 31
gagcctctca tatctggatc tctaaatc 28

<210> SEQ ID NO 32
<211> LENGTH: 31
<212> TYPE: DNA
<213> ORGANISM: artificial sequence
<220> FEATURE:
<223> OTHER INFORMATION: probe
<220> FEATURE:
<221> NAME/KEY: misc_feature
<222> LOCATION: (1)..(31)

<400> SEQUENCE: 32
ttaactagca gtcatctgtc ctgtgccaag g 31

<210> SEQ ID NO 33
<211> LENGTH: 27
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(27)

<400> SEQUENCE: 33
gacaaactct accaaggaga gacaaaa 27

<210> SEQ ID NO 34
<211> LENGTH: 26
<212> TYPE: DNA
<213> ORGANISM: artificial sequence -continued
<220> FEATURE:
<223> OTHER INFORMATION: primer
<220> FEATURE:
<221> NAME/KEY: miisc_feature
<222> LOCATION: (1)..(26)

<400> SEQUENCE: 34
ctaccaagga gagacaaaac acaaaa 26

<210> SEQ ID NO 35
<211> LENGTH: 26
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(26)

<400> SEQUENCE: 35
tcttgtgaga ctgcatggac tagagt 26

<210> SEQ ID NO 36
<211> LENGTH: 25
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(25)

<400> SEQUENCE: 36
gatcttgtga gactgcatgg actag 25

<210> SEQ ID NO 37
<211> LENGTH: 32
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(32)

<400> SEQUENCE: 37
catgcgagaa ttaaagagct atagttgcgt gc 32

<210> SEQ ID NO 38
<211> LENGTH: 23
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(23)

<400> SEQUENCE: 38
cgcaatcctt tctcgacttc taa 23

<210> SEQ ID NO 39
<211> LENGTH: 23
<212> TYPE: DNA
<213> ORGANISM: artificial sequence
<220> FEATURE:
<223> OTHER INFORMATION: primer
<220> FEATURE:
<221> NAME/KEY: misc_feature -continued

<222> LOCATION: (1)..(23)

<400> SEQUENCE: 39
gtttcgcaat cctttctcga ctt 23

<210> SEQ ID NO 40
<211> LENGTH: 21
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(21)

<400> SEQUENCE: 40
gcagaattcg cccttaagtc g 21

<210> SEQ ID NO 41
<211> LENGTH: 21
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(21)

<400> SEQUENCE: 41
tctgcagaat tcgcccttaa g 21

<210> SEQ ID NO 42
<211> LENGTH: 25
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(25)

<400> SEQUENCE: 42
aaggtagccg tatcggaagg tgcgg 25

<210> SEQ ID NO 43
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 43
ccagaacgga ggtgatccag 20

<210> SEQ ID NO 44
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 44

-continued

```
ttccagaacg gaggtgatcc                                                    20


<210> SEQ ID NO 45
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 45

atattcttgc tgaattggtc                                                    20


<210> SEQ ID NO 46
<211> LENGTH: 25
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(25)

<400> SEQUENCE: 46

caaaattatt tcatccttgg cacag                                              25


<210> SEQ ID NO 47
<211> LENGTH: 24
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(24)

<400> SEQUENCE: 47

aaattatttc atccttggca cagg                                               24


<210> SEQ ID NO 48
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 48

atattcttgc tgaattggtc                                                    20


<210> SEQ ID NO 49
<211> LENGTH: 25
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(25)

<400> SEQUENCE: 49

agatgggcag agtgtagatc ttgtg                                              25


<210> SEQ ID NO 50
```

-continued

<211> LENGTH: 25
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(25)

<400> SEQUENCE: 50
ggaaccgaga gagtagcaac agaac 25

<210> SEQ ID NO 51
<211> LENGTH: 24
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(24)

<400> SEQUENCE: 51
caggaaccga gagagtagca acag 24

<210> SEQ ID NO 52
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 52
gcgttcggct tgaagtcatg 20

<210> SEQ ID NO 53
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 53
cctttggtcg ggtgggagaa 20

<210> SEQ ID NO 54
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 54
gccaggctga atcttgggaa 20

<210> SEQ ID NO 55
<211> LENGTH: 20
<212> TYPE: DNA
<213> ORGANISM: artificial sequence
<220> FEATURE:

<223> OTHER INFORMATION: primer
<220> FEATURE:
<221> NAME/KEY: misc_feature
<222> LOCATION: (1)..(20)

<400> SEQUENCE: 55
ccaggctgaa tcttgggaaa 20

<210> SEQ ID NO 56
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 56
ccaagtacgc atctcggatg 20

<210> SEQ ID NO 57
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 57
gaagtgttta ctctttgccg 20

<210> SEQ ID NO 58
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 58
aatattggtt cttgatcctg 20

<210> SEQ ID NO 59
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 59
tcgagacaat agagattttc 20

<210> SEQ ID NO 60
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

-continued

<400> SEQUENCE: 60
tcgagacaat agagattttc 20

<210> SEQ ID NO 61
<211> LENGTH: 22
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(22)

<400> SEQUENCE: 61
acataccatc ttgtaaatag cc 22

<210> SEQ ID NO 62
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 62
catagtcaat ccaagctttc 20

<210> SEQ ID NO 63
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 63
ataccatctt gtaaatagcc 20

<210> SEQ ID NO 64
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 64
tatgcttctg gtctttgttt 20

<210> SEQ ID NO 65
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 65
aatcaatgtc atgcggttcg 20

-continued

<210> SEQ ID NO 66
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 66
cacttccacg gcagtgataa 20

<210> SEQ ID NO 67
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 67
ttgtctcttg ggtaatcatg 20

<210> SEQ ID NO 68
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 68
gtgccaaaag gaactgattg 20

<210> SEQ ID NO 69
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 69
tgagattccg gactgcattt 20

<210> SEQ ID NO 70
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 70
caaactgaga tttctcaacg 20

<210> SEQ ID NO 71
<211> LENGTH: 20

-continued

<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 71
ccttacccga cctgccatgt 20

<210> SEQ ID NO 72
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 72
ctggcggcca tatcgacttc 20

<210> SEQ ID NO 73
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 73
attagcaact ggaatgcaca 20

<210> SEQ ID NO 74
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 74
aagccagctg catgatgttc 20

<210> SEQ ID NO 75
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 75
cgccctagca catcatcaaa 20

<210> SEQ ID NO 76
<211> LENGTH: 20
<212> TYPE: DNA
<213> ORGANISM: artificial sequence
<220> FEATURE:
<223> OTHER INFORMATION: primer -continued

```
<220> FEATURE:
<221> NAME/KEY: misc_feature
<222> LOCATION: (1)..(20)

<400> SEQUENCE: 76

cctagcacat catcaaaaga                                                20


<210> SEQ ID NO 77
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)

<400> SEQUENCE: 77

ggagcatgga agcactcgta                                                20
```